(12) United States Patent
Nishioka et al.

(10) Patent No.: US 6,646,156 B2
(45) Date of Patent: Nov. 11, 2003

(54) (METH)ACRYLOYL-GROUP-CONTAINING CARBAMOYL HALIDES AND PRODUCTION PROCESS THEREFOR

(75) Inventors: Ayako Nishioka, Chiba (JP); Kaneo Nozawa, Fukushima (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/835,321

(22) Filed: Apr. 17, 2001

(65) Prior Publication Data

US 2002/0013492 A1 Jan. 31, 2002

Related U.S. Application Data

(60) Provisional application No. 60/272,475, filed on Mar. 2, 2001.

(30) Foreign Application Priority Data

Apr. 17, 2000 (JP) .................................... 2000-115479
Mar. 19, 2001 (JP) .................................... 2001-078125

(51) Int. Cl.$^7$ ............................................. C07C 69/52
(52) U.S. Cl. .................................... 560/222; 562/172
(58) Field of Search ........................... 562/172; 560/222

(56) References Cited

FOREIGN PATENT DOCUMENTS

FR          1432865      *   3/1966

OTHER PUBLICATIONS

CA 64:111109, of French patent 1432865.*

* cited by examiner

Primary Examiner—Alan L. Rotman
Assistant Examiner—Hector Reyes
(74) Attorney, Agent, or Firm—Sughrue Mion, PLLC

(57) ABSTRACT

The present invention provides a (meth)acryloyl-group-containing carbamoyl halide represented by the following formula (1):

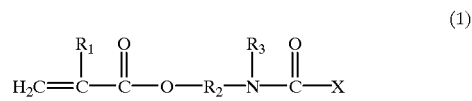

where $R_1$ represents a hydrogen atom or a methyl group; $R_2$ represents a linear or branched C1–C10 alkylene group; $R_3$ represents a C1–C5 alkyl group; and X represents a halogen atom. The present invention also provides a production process for the halide.

11 Claims, 4 Drawing Sheets under
(METH)ACRYLOYL-GROUP-CONTAINING CARBAMOYL HALIDES AND PRODUCTION PROCESS THEREFOR

CROSS REFERENCE TO RELATED APPLICATIONS

This application is an application filed under 35 U.S.C. §111(a) claiming benefit pursuant to 35 U.S.C. §119(e)(1) of the filing date of Provisional Application 60/272,475 filed Mar. 2, 2001 pursuant to 35 U.S.C. §111(b).

FIELD OF THE INVENTION

The present invention relates to a (meth)acryloyl-group-containing carbamoyl halide; a process for producing the halide; a salt of a (meth)acryloyl-group-containing amine serving as an intermediate of the halide; and a process for producing the salt. The (meth)acryloyl-group-containing carbamoyl halide is useful as a monomer for forming resins in the production of a variety of industrial products, including electronic materials, resist ink, plastic lenses, and paints. The halide can also be transformed into a macromonomer through reaction with an active-hydrogen-containing compound, such as a compound containing a hydroxyl group or an amino group, thereby imparting various useful functions to resins.

BACKGROUND OF THE INVENTION

As described above, a compound containing a carbon—carbon double bond and a functional group, such as an isocyanate group, a chlorocarbonyl group, or an epoxy group, effectively works to impart various functions to resins. Typical examples of such compounds include 2-methacryloyloxyethyl isocyanate represented by the following formula (4):

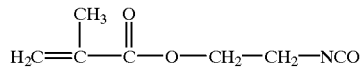

(4)

which contains two functional groups; i.e., a methacryloyl group and an isocyanate group, and 2-methacryloyloxyethylcarbamoyl chloride represented by the following formula (5):

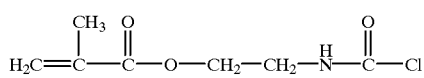

(5)

which is a compound obtained through addition of hydrochloric acid to 2-methacryloyloxyethyl isocyanate.

These compounds are useful in that they can impart various functions to resins. However, when such a compound is reacted with another compound having active hydrogen, a product having an —NH— group is formed, and in some cases, the —NH— group contained in the product may cause deterioration of the characteristics of resins. One conceivable measure to prevent such deterioration is the use of an N,N-disubstituted compound containing a carbon—carbon double bond and a functional group.

However, no researchers have hitherto reported that an N,N-disubstituted compound containing a carbon—carbon double bond and a functional group has been obtained, presumably due to difficulty in purification of the compound.

SUMMARY OF THE INVENTION

In view of the foregoing, an object of the present invention is to provide a novel (meth)acryloyl-group-containing carbamoyl halide, which is an N,N-disubstituted compound containing a carbon—carbon double bond and a functional group.

Another object of the present invention is to provide a process for producing the halide; particularly, a (meth)acryloyl-group-containing carbamoyl halide of high purity.

Yet another object of the present invention is to provide a novel (meth)acryloyl-group-containing amine salt which is used as a raw material for producing the (meth)acryloyl-group-containing carbamoyl halide, as well as a process for producing the salt.

The present inventors have found that, when a salt of a (meth)acryloyl-group-containing amine represented by the following formula (2):

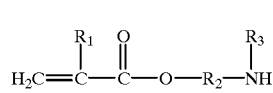

(2)

(wherein $R_1$ represents a hydrogen atom or a methyl group; $R_2$ represents a linear or branched C1–C10 alkylene group; and $R_3$ represents a C1–C5 alkyl group) is purified through, for example, recrystallization, and the purity of the salt is increased satisfactorily, reaction between the salt and a carbonyl dihalide proceeds with high selectivity, and a (meth)acryloyl-group-containing carbamoyl halide represented by the following formula (1):

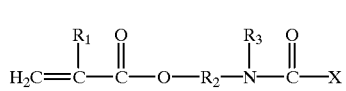

(1)

(wherein $R_1$ represents a hydrogen atom or a methyl group; $R_2$ represents a linear or branched C1–C10 alkylene group; $R_3$ represents a C1–C5 alkyl group; and X represents a halogen atom) with very high purity can be produced. The present invention has been accomplished on the basis of this finding.

Accordingly, a first embodiment of the present invention provides a (meth)acryloyl-group-containing carbamoyl halide represented by the following formula (1):

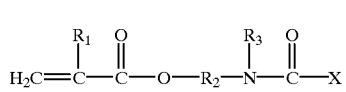

(1)

wherein $R_1$ represents a hydrogen atom or a methyl group; $R_2$ represents a linear or branched C1–C10 alkylene group; $R_3$ represents a C1–C5 alkyl group; and X represents a halogen atom.

Preferably, $R_2$ is —$CH_2CH_2$—, —$(CH_2)_3$—, —$(CH_2)_4$—, —$CH_2CH(CH_3)$—, —$CH(CH_3)CH_2$—, —$CH(CH_3)CH(CH_3)$—, —$CH_2C(CH_3)_2$—, or —$C(CH_3)_2CH_2$—; $R_3$ is a methyl group, an ethyl group, a propyl group, an isopropyl group, a butyl group, an isobutyl group, a sec-butyl group, or a tert-butyl group; and X is a chlorine or bromine atom.

Preferably, the (meth)acryloyl-group-containing carbamoyl halide is N-methyl-N-(2-methacryloyloxyethyl) carbamoyl chloride.

A second embodiment of the present invention provides a salt of a (meth)acryloyl-group-containing amine represented by the following formula (2):

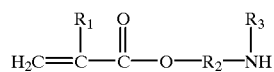
(2)

wherein $R_1$ represents a hydrogen atom or a methyl group; $R_2$ represents a linear or branched C1–C10 alkylene group; and $R_3$ represents a C1–C5 alkyl group.

Preferably, an acid for forming the salt of the (meth)acryloyl-group-containing amine is any one of hydrogen chloride, hydrogen bromide, sulfuric acid, nitric acid, and trifluoroacetic acid.

Preferably, $R_2$ is —CH$_2$CH$_2$—, —(CH$_2$)$_3$—, —(CH$_2$)$_4$—, —CH$_2$CH(CH$_3$)—, —CH(CH$_3$)CH$_2$—, —CH(CH$_3$)CH(CH$_3$)—, —CH$_2$C(CH$_3$)$_2$—, or —C(CH$_3$)$_2$CH$_2$—; and $R_3$ is a methyl group, an ethyl group, a propyl group, an isopropyl group, a butyl group, an isobutyl group, a sec-butyl group, or a tert-butyl group.

Preferably, the salt of the (meth)acryloyl-group-containing amine is N-methyl-N-(2-methacryloyloxyethyl) amine hydrochloride.

A third embodiment of the present invention provides a process for producing a (meth)acryloyl-group-containing carbamoyl halide represented by the following formula (1):

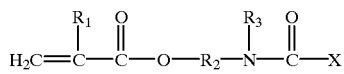
(1)

(wherein $R_1$ represents a hydrogen atom or a methyl group; $R_2$ represents a linear or branched C1–C10 alkylene group; $R_3$ represents a C1–C5 alkyl group; and X represents a halogen atom), which process comprises reacting a carbonyl dihalide with a salt of a (meth)acryloyl-group-containing amine represented by the following formula (2):

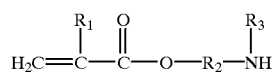
(2)

wherein $R_1$ represents a hydrogen atom or a methyl group; $R_2$ represents a linear or branched C1–C10 alkylene group; and $R_1$ represents a C1–C5 alkyl group.

Preferably, an acid for forming the salt of the (meth)acryloyl-group-containing amine is any one of hydrogen chloride, hydrogen bromide, sulfuric acid, nitric acid, and trifluoroacetic acid.

Preferably, $R_2$ is —CH$_2$CH$_2$—, —(CH$_2$)$_3$—, —(CH$_2$)$_4$—, —CH$_2$CH(CH$_3$)—, —CH(CH$_3$)CH$_2$—, —CH(CH$_3$)CH(CH$_3$)—, —CH$_2$C(CH$_3$)$_2$—, or —C(CH$_3$)$_2$CH$_2$—; and $R_3$ is a methyl group, an ethyl group, a propyl group, an isopropyl group, a butyl group, an isobutyl group, a sec-butyl group, or a tert-butyl group.

Preferably, the salt of the (meth)acryloyl-group-containing amine is N-methyl-N-(2-methacryloyloxyethyl) amine hydrochloride, and the (meth)acryloyl-group-containing carbamoyl halide is N-methyl-N-(2-methacryloyloxy-ethyl)carbamoyl chloride.

Preferably, a purified (meth)acryloyl-group-containing amine salt is used, and more preferably, the (meth)acryloyl-group-containing amine salt is purified through recrystallization.

Preferably, a solvent mixture of a good solvent and a poor solvent of the (meth)acryloyl-group-containing amine salt is used for recrystallization.

Preferably, the carbonyl dihalide is carbonyl chloride or a carbonyl chloride precursor.

A fourth embodiment of the present invention provides a process for producing a salt of a (meth)acryloyl-group-containing amine represented by the following formula (2):

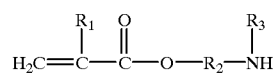
(2)

(wherein $R_1$ represents a hydrogen atom or a methyl group; $R_2$ represents a linear or branched C1–C10 alkylene group; and $R_3$ represents a C1–C5 alkyl group), which process comprises reacting a (meth)acrylic acid derivative with a hydrochloride, hydrobromide, sulfate, nitrate, or trifluoroacetate of an amine represented by the following formula (3):

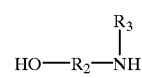
(3)

wherein $R_2$ represents a linear or branched C1–C10 alkylene group; and $R_3$ represents a C1–C5 alkyl group.

Preferably, $R_2$ is —CH$_2$CH$_2$—, —(CH$_2$)$_3$—, —(CH$_2$)$_4$—, —CH$_2$CH(CH$_3$)—, —CH(CH,)CH$_2$—, —CH(CH$_3$)CH(CH$_3$)—, —CH$_2$C(CH$_3$)$_2$—; or —C(CH$_3$)$_2$CH$_2$—; and $R_3$ is a methyl group, an ethyl group, a propyl group, an isopropyl group, a butyl group, an isobutyl group, a sec-butyl group, or a tert-butyl group.

Preferably, the (meth)acrylic acid derivative is a (meth)acrylic acid halide.

Preferably, in the process for producing a (meth)acryloyl-group-containing carbamoyl halide according to the third embodiment, a salt of a (meth)acryloyl-group-containing amine produced through a production process as recited in the fourth embodiment is used.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with accompanying drawings, in which.

DESCRIPTION OF THE PREFERRED EMBODIMENTS

Figure 1:
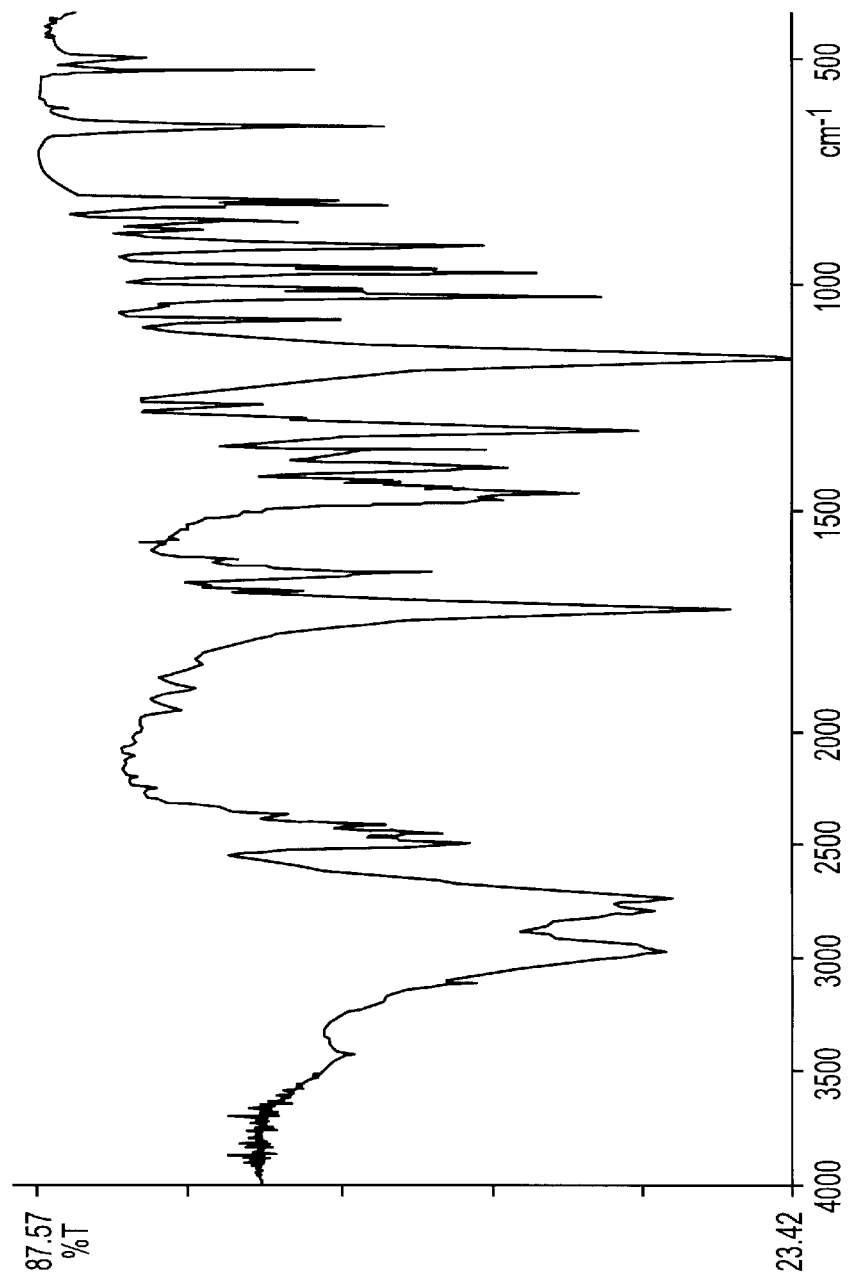
FIG. 1 shows an infrared spectrum of N-methyl-N-(2-methacryloyloxyethyl) amine hydrochloride.

As used herein, the term "(meth)acryloyl" refers to "methacryloyl" and/or "acryloyl."

The (meth)acryloyl-group-containing carbamoyl halide of the present invention is a compound represented by the following formula (1):

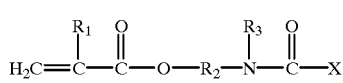

(1)

(wherein $R_1$ represents a hydrogen atom or a methyl group; $R_2$ represents a linear or branched C1–C10 alkylene group; $R_3$ represents a C1–C5 alkyl group; and X represents a halogen atom). Preferably, $R_2$ is —$CH_2CH_2$—, —$(CH_2)_3$—, —$(CH_2)_4$—, —$CH_2CH(CH_3)$—, —$CH(CH_3)CH_2$—, —$CH(CH_3)CH(CH_3)$—, —$CH_2C(CH_3)_2$—, or —$C(CH_3)_2CH_2$—; $R_3$ is a methyl group, an ethyl group, a propyl group, an isopropyl group, a butyl group, an isobutyl group, a sec-butyl group, or a tert-butyl group; and X is a chlorine or bromine atom. From the viewpoints of chemical stability and ease of procurement of the raw material for producing the compound, a particularly preferred halide is N-methyl-N-(2-methacryloyloxyethyl)carbamoyl chloride.

The salt of the (meth)acryloyl-group-containing amine of the present invention can be used as a raw material for producing the (meth)acryloyl-group-containing carbamoyl halide, and is represented by the following formula (2):

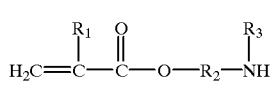

(2)

wherein $R_1$ represents a hydrogen atom or a methyl group; $R_2$ represents a linear or branched C1–C10 alkylene group; and $R_3$ represents a C1–C5 alkyl group. Examples of acids for forming the salt include hydrogen chloride, hydrogen bromide, sulfuric acid, nitric acid, and trifluoroacetic acid. Of these, hydrogen chloride is preferred. Preferably, $R_2$ is —$CH_2CH_2$—, —$(CH_2)_3$—, —$(CH_2)_4$—, —$CH_2CH(CH_3)$—, —$CH(CH_3)CH_2$—, —$CH(CH_3)CH(CH_3)$—, —$CH_2C(CH_3)_2$—, or —$C(CH_3)_2CH_2$—; and $R_3$ is a methyl group, an ethyl group, a propyl group, an isopropyl group, a butyl group, an isobutyl-group, a sec-butyl group, or a tert-butyl group. From the viewpoints of chemical stability and ease of procurement of the raw material for producing the salt, a particularly preferred salt is N-methyl-N-(2-methacryloyloxyethyl)amine hydrochloride.

The (meth)acryloyl-group-containing carbamoyl halide represented by formula (1) is produced through the following procedure: a carbonyl dihalide is reacted, in a solvent, with a salt of the (meth)acryloyl-group-containing amine represented by formula (2), which is purified; and the solvent is removed from the resultant reaction mixture.

When the (meth)acryloyl-group-containing carbamoyl halide is produced, an acid corresponding to the raw material; i.e., the (meth)acryloyl-group-containing amine salt, is produced as a by-product. Therefore, after completion of reaction, the acid must be removed from the resultant reaction mixture. In the case in which the boiling point of the acid by-product is low, when the solvent is removed from the reaction mixture, the acid is also removed therefrom. In contrast, in the case in which the boiling point of the acid by-product is high, the acid is removed, for example, by adding water to the resultant reaction mixture for transferring the acid into an aqueous phase, and separating the aqueous phase from the reaction mixture to remove the acid from the reaction mixture.

Any solvent may be used in the reaction, so long as the solvent dissolves the raw material and the product and has no reactivity therewith. Examples of such a solvent include toluene, benzene, methylene chloride, chloroform, ether, ethyl acetate, and tetrahydrofuran.

Examples of carbonyl dihalides used for producing the (meth)acryloyl-group-containing carbamoyl halide include carbonyl chloride, carbonyl dibromide, and chlorocarbonyl bromide. Of these, carbonyl chloride is preferably used. A carbonyl chloride precursor which readily forms carbonyl chloride through, for example, heating, such as carbonyl chloride dimer, may also be used.

The reaction may be carried out at a temperature within a range of 0° C. to the boiling point of the solvent employed. Preferably, the reaction is carried out at a temperature within a range of 30° C. to the boiling point of the solvent. The reaction time varies depending on the reaction temperature. The upper limit of the reaction time is 10 hours from the completion of addition of the carbonyl halide.

The (meth)acryloyl-group-containing amine salt used for producing the (meth)acryloyl-group-containing carbamoyl halide may be produced through the below-described production process, or through other production processes. Alternatively, the (meth)acryloyl-group-containing amine salt may be purified through a purification technique such as recrystallization. The salt serving as a raw material of the (meth)acryloyl-group-containing carbamoyl halide is preferably purified, since the halide is chemically unstable and is not purified through a customary technique such as distillation. When the salt is purified, the selectivity of the reaction is enhanced, and thus (meth)acryloyl-group-containing carbamoyl halide of high purity can be produced. When an unpurified (meth)acryloyl-group-containing amine salt is used, the resultant (meth)acryloyl-group-containing carbamoyl halide may fail to have high purity.

The (meth)acryloyl-group-containing amine salt is purified through recrystallization from a solvent mixture of a poor solvent of the salt and a good solvent of the salt. Examples of the poor solvent include acetone, ethyl acetate, toluene, methylene chloride, benzene, hexane, chloroform, ether, tetrahydrofuran, and dioxane. Examples of the good solvent include water, methanol, ethanol, isopropyl alcohol, dimethylformamide, and dimethyl sulfoxide. The mixing ratio of the poor solvent to the good solvent is 1:1–100:1, preferably, 7:3–20:1.

The (meth)acryloyl-group-containing amine salt is produced as follows. A (meth)acrylic acid derivative and a salt of an amine represented by the following formula (3):

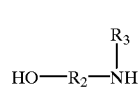

(3)

(wherein $R_2$ represents a linear or branched C1–C10 alkylene group; and $R_3$ represents a C1–C5 alkyl group) are placed in a reactor containing a solvent, the resultant mixture is stirred to react, and then the resultant reaction mixture is subjected to known processes, including concentration and filtration. Any acid may be used for forming a salt of the amine of formula (3), so long as the acid is sufficiently strong that it can prevent the reaction between the (meth)acrylic acid derivative and the NH site of the amine of formula (3) during the reaction between the salt and the derivative. Preferred examples of such an acid include hydrogen chloride, hydrogen bromide, sulfuric acid, nitric acid, and trifluoroacetic acid. Of these, hydrogen chloride is more preferred. Preferably, $R_2$ is —$CH_2CH_2$—, —$(CH_2)_3$—, —$(CH_2)_4$—, —$CH_2CH(CH_3)$—, —$CH(CH_3)CH_2$—, —$CH(CH_3)CH(CH_3)$—, —$CH_2C(CH_3)_2$—, or —$C(CH_3)CH_2$—; and $R_3$ is a methyl group, an ethyl group, a propyl group, an isopropyl group, a butyl group, an isobutyl group, a sec-butyl group, or a tert-butyl group. Examples of preferred (meth)acrylic acid derivatives include (meth)acryloyl halides such as methacryloyl chloride.

EXAMPLES

The present invention will next be described in more detail by way of Examples, which should not be construed as limiting the invention thereto. Unless indicated otherwise herein, all parts, percents, ratios and the like are by weight.

Example 1

Synthesis of N-methyl-N-(2-methacryloyloxyethyl) amine Hydrochloride 2-(Methylamino)ethanol (60.0 g, 0.80 mol) was dissolved in toluene (500 ml) and heated to 80° C. HCl gas (32.1 g, 0.88 mol) was introduced into the resultant solution over two hours. After introduction was complete, the resultant mixture was stirred for one hour to allow the reaction to proceed. Subsequently, excess HCl gas was purged from the resultant reaction mixture by use of nitrogen.

The reaction mixture was heated to 80° C., and methacryloyl chloride (92.0 g, 0.88 mol) was added dropwise to the mixture over one hour while the mixture was stirred. The resultant reaction mixture was further stirred at 80° C. for one hour to allow the reaction to proceed. During reaction, N-methyl-N-(2-methacryloyloxyethyl)amine hydrochloride was precipitated.

Figure 2:
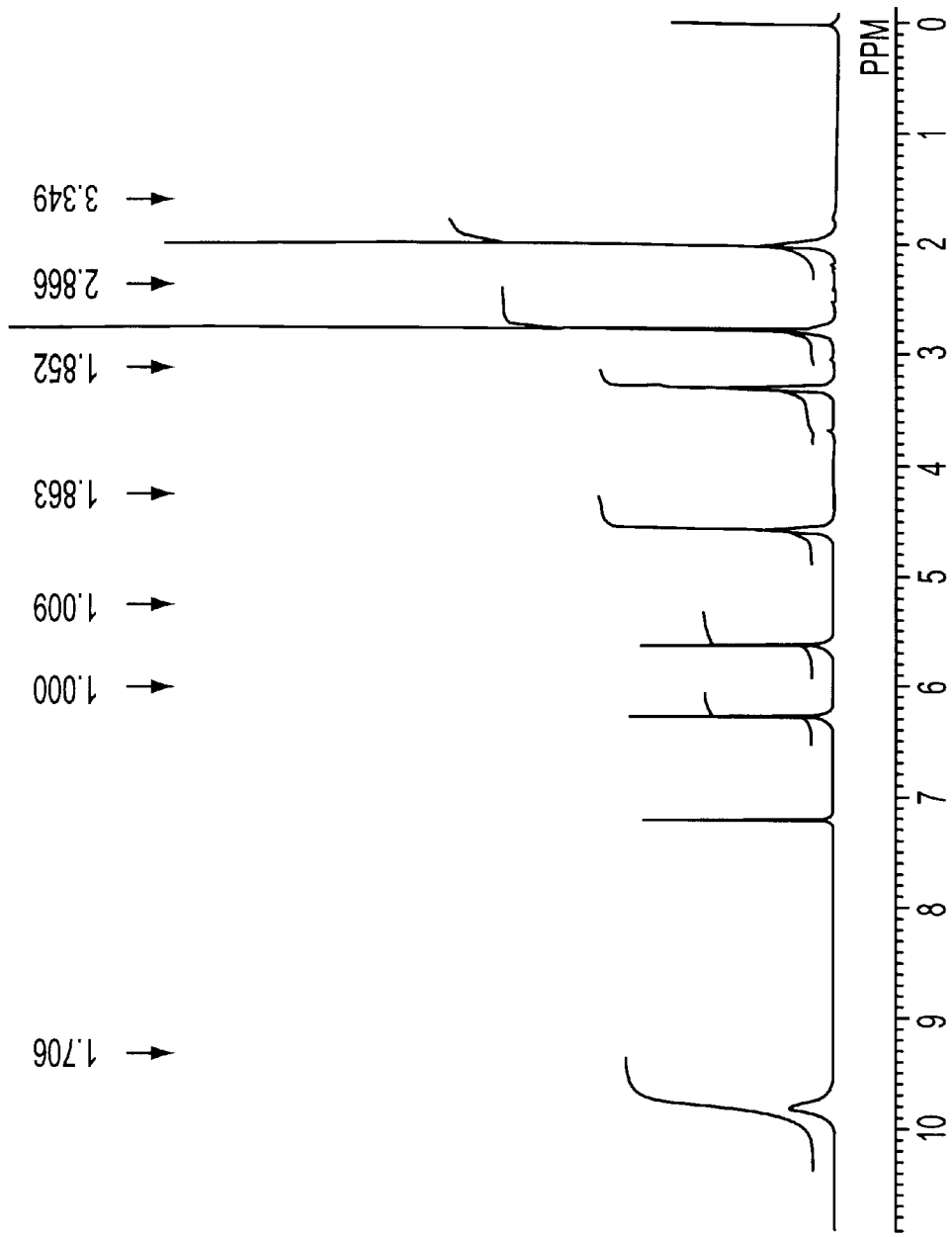
FIG. 2 shows an NMR spectrum of N-methyl-N-(2-methacryloyloxyethyl) amine hydrochloride.

After reaction was complete, the resultant reaction mixture was cooled to 20° C., and crystals that precipitated were subjected to filtration, collection, and then washing with toluene (100 ml). The thus-obtained crude crystals of N-methyl-N-(2-methacryloyloxyethyl)amine hydrochloride were recrystallized from a solvent mixture of acetone/methanol (10/1), subjected to filtration, collection, and then drying to produce N-methyl-N-(2-methacryloyloxyethyl) amine hydrochloride (95.0 g, 0.529 mol, yield: 66%). The product was analyzed through liquid chromatography (column: SHODEX_DM-614, eluent: an aqueous solution of phosphoric acid (0.1 mass %)/sodium octanesulfonate (0.005 mol/L)), and the purity of the product was found to be 99% or more. FIGS. 1 and 2 show the infrared spectrum and NMR spectrum of the product, respectively.

IR (cm$^{-1}$): 1161, 1322, 1634, 1719, 2729, 2788, 2964

NMR (CDCl$_3$): 2.00 ppm (s, 3H), 2.80 ppm (s, 3H), 3.35 ppm (t, 2H), 4.60 ppm (t, 2H), 5.70 ppm (s, 1H), 6.35 ppm (s, 1H)

Example 2

Synthesis of N-methyl-N-(2-methacryloyloxyethyl) carbamoyl chloride

Figure 3:
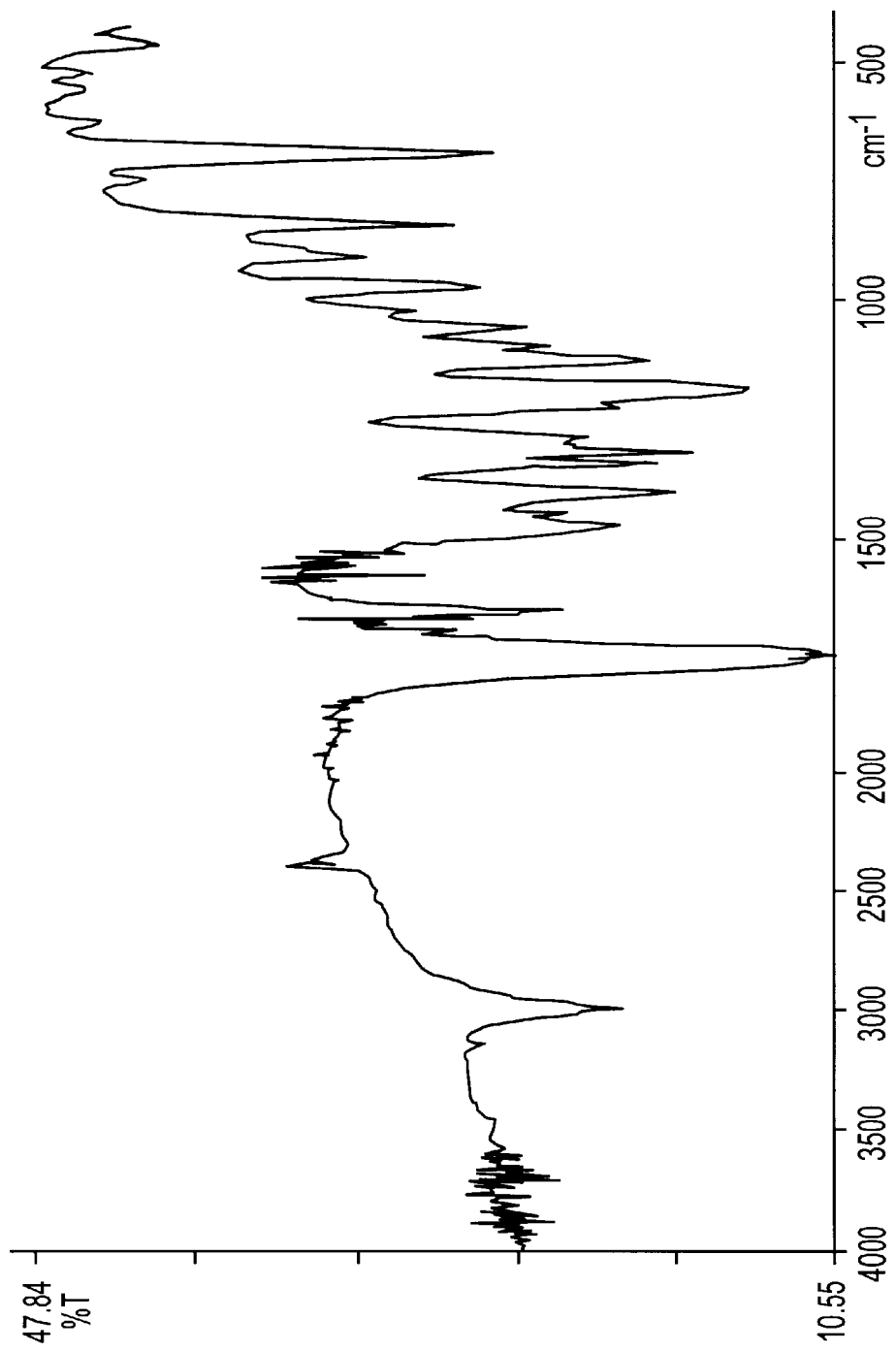
FIG. 3 shows an Infrared spectrum of N-methyl-N-(2-methacryloyloxy-ethyl)carbamoyl chloride.
Figure 4:
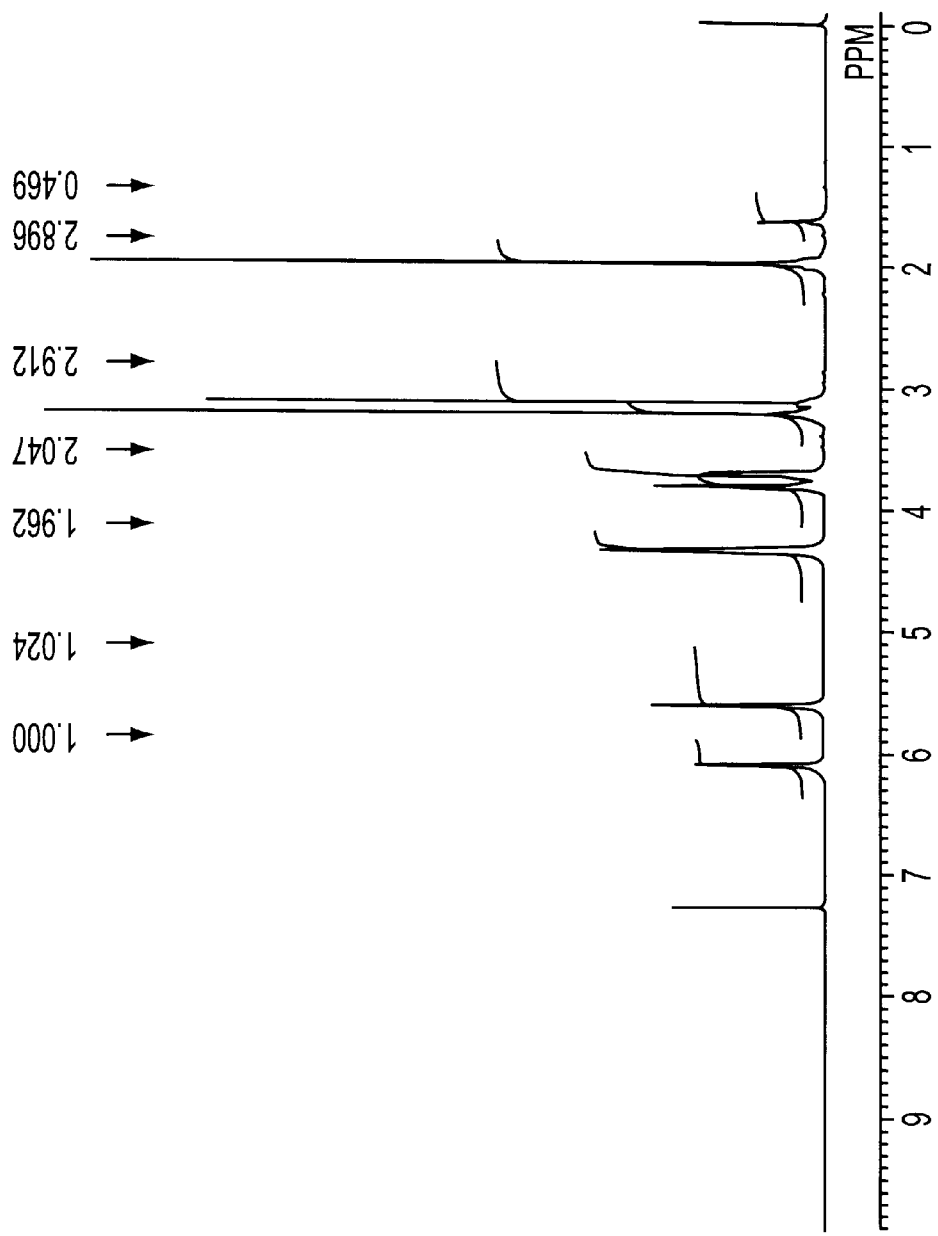
FIG. 4 shows an NMR spectrum of N-methyl-N-(2-methacryloyloxy-ethyl)carbamoyl chloride.

N-Methyl-N-(2-methacryloyloxyethyl)amine hydrochloride (95.0 g, 0.529 mol) produced in Example 1 was suspended in methylene chloride (300 ml) and heated to 50° C. Phosgene (7.85 g, 0.793 mol) was introduced into the resultant suspension over two hours. The resultant reaction mixture was further stirred for one hour, and then the methylene chloride was removed from the mixture to produce N-methyl-N-(2-methacryloyloxyethyl)carbamoyl chloride (106.6 g, almost quantitative yield, purity: 98%) as a colorless transparent liquid. The product was analyzed through gas chromatography (column: silicone SE-30 20% glass column (2 m), injection temperature: 220° C., detection temperature: 230° C.). FIGS. 3 and 4 show the infrared spectrum and NMR spectrum of the product, respectively.

IR (cm$^{-1}$): 1163, 1637, 1732

NMR (CDCl$_3$): 2.00 ppm (s, 3H), 3.15 ppm (d, 3H), 3.80 ppm (m, 2H), 4.38 ppm (m, 2H), 5.65 ppm (s, 1H), 6.15 ppm (d, 1H)

The (meth)acryloyl-group-containing carbamoyl halide of the present invention is useful as a monomer for forming resins used for producing a variety of industrial products, including electronic materials, resist ink, plastic lenses, and paints.

While the invention has been described in detail and with reference to specific embodiments thereof, it will be apparent to one skilled in the art that various changes and modifications can be made therein without departing from the spirit and scope thereof.

What is claimed is:

1. A process for producing a (meth)acryloyl-group-containing carbamoyl halide represented by the following formula (1):

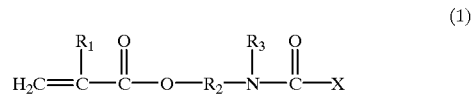

(1)

wherein $R_1$ represents a hydrogen atom or a methyl group; $R_2$ represents a linear or branched C1–C$_{10}$ alkylene group; $R_3$ represents a C1–C5 alkyl group; and X represents a halogen atom, which process comprises reacting a carbonyl dihalide with a salt of a (meth)acryloyl-group-containing amine represented by the following formula (2):

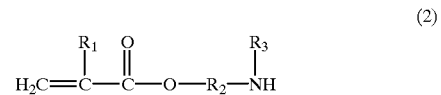

(2)

wherein $R_1$ represents a hydrogen atom or a methyl group; $R_2$ represents a linear or branched C1–C10 alkylene group; and $R_3$ represents a C1–C5 alkyl group.

2. The process for producing a (meth)acryloyl-group-containing carbamoyl halide according to claim 1, wherein an acid for forming the salt of the (meth)acryloyl-group-containing amine is one selected from the group consisting of hydrogen chloride, hydrogen bromide, sulfuric acid, nitric acid, and trifluoroacetic acid.

3. The process for producing a (meth)acryloyl-group-containing carbamoyl halide according to claim 1, wherein $R_2$ is —$CH_2CH_2$—, —$(CH_2)_3$—, —$(CH_2)_4$—, —$CH_2CH(CH_3)$—, —$CH(CH_3)CH_2$—, —$CH(CH_3)CH(CH_3)$—, —$CH_2C(CH_3)_2$—, or —$C(CH_3)_2CH_2$—; and $R_3$ is a methyl group, an ethyl group, a propyl group, an isopropyl group, a butyl group, an isobutyl group, a sec-butyl group, or a tert-butyl group.

4. The process for producing a (meth)acryloyl-group-containing carbamoyl halide according to claim 1, wherein the salt of the (meth)acryloyl-group-containing amine is N-methyl-N-(2-methacryloyloxyethyl)amine hydrochloride, and the (meth)acryloyl-group-containing carbamoyl halide is N-methyl-N-(2-methacryloyloxyethyl)carbamoyl chloride.

5. The process for producing a (meth)acryloyl-group-containing carbamoyl halide according to claim 1, wherein the salt of the (meth) acryloyl-group-containing amine is a purified salt.

6. The process for producing a (meth)acryloyl-group-containing carbamoyl halide according to claim 5, wherein the (meth)acryloyl-group-containing amine salt is a salt purified through recrystallization.

7. The process for producing a (meth)acryloyl-group-containing carbamoyl halide according to claim 6, wherein the recrystallization is carried out using a solvent mixture of a solvent in which the (meth)acryloyl-group containing amine salt is soluble and a solvent in which the salt is slightly soluble or insoluble.

8. The process for producing a (meth)acryloyl-group-containing carbamoyl halide according to claim 7, wherein the solvent in which the (meth)acryloyl-group-containing amine salt is soluble is selected from the group consisting of water, methanol, ethanol, isopropyl alcohol, dimethylformamide, and dimethyl sulfoxide.

9. The process for producing a (meth)acryloyl-group-containing carbamoyl halide according to claim 7, wherein the solvent in which the salt is slightly soluble or insoluble is selected from the group consisting of acetone, ethyl acetate, toluene, methylene chloride, benzene, hexane, chloroform, ether, tetrahydrofuran, and dioxane.

10. The process for producing a (meth)acryloyl-group-containing carbamoyl halide according to claim 1, wherein the carbonyl dihalide is carbonyl chloride or a carbonyl chloride precursor.

11. A process for producing a (meth)acryloyl-group-containing carbamoyl halide represented by the following formula (1):

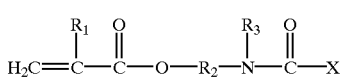
(1)

wherein $R_1$ represents a hydrogen atom or a methyl group; $R_2$ represents a linear or branched C1–C10 alkylene group; $R_3$ represents a C1–C5 alkyl group; and X represents a halogen atom, which process comprises reacting a carbonyl dihalide with a salt of a (meth)acryloyl-group-containing amine represented by the following formula (2):

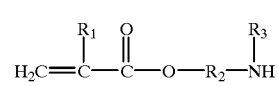
(2)

wherein $R_1$ represents a hydrogen atom or a methyl group; $R_2$ represents a linear or branched C1–C10 alkylene group; and $R_3$ represents a C1–C5 alkyl group, wherein a salt of a (meth)acryloyl-group-containing amine represented by formula (2) produced by reacting a (meth)acrylic acid derivative with a hydrochloride, hydrobromide, sulfate, nitrate, or trifluoroacetate of an amine represented by the following formula (3):

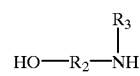
(3)

wherein $R_2$ represents a linear or branched C1–C10 alkylene group, and $R_3$ represents a C1–C5 alkyl group is used.

* * * * *